United States Patent [19]
Copeland

[11] Patent Number: 5,976,150
[45] Date of Patent: Nov. 2, 1999

[54] INTRAOCULAR LENS INJECTION SYSTEM

[75] Inventor: Barry L. Copeland, Arlington, Tex.

[73] Assignee: Alcon Laboratories, Inc.

[21] Appl. No.: 09/139,387

[22] Filed: Aug. 25, 1998

[51] Int. Cl.$^6$ .................................. A61F 9/00; A61F 2/16
[52] U.S. Cl. ............................................... 606/107; 623/6
[58] Field of Search ................................. 606/107; 623/6

[56] References Cited

U.S. PATENT DOCUMENTS

| | | | |
|---|---|---|---|
| 4,573,998 | 3/1986 | Mazzocco | 623/6 |
| 4,681,102 | 7/1987 | Bartell . | |
| 4,747,404 | 5/1988 | Jampel et al. . | |
| 4,759,763 | 7/1988 | Bissonette et al. | 623/6 |
| 4,834,094 | 5/1989 | Patton et al. . | |
| 4,836,201 | 6/1989 | Patton et al. . | |
| 4,919,130 | 4/1990 | Stoy et al. | 606/107 |
| 5,007,913 | 4/1991 | Dulebohn et al. | 606/107 |
| 5,171,241 | 12/1992 | Buboltz et al. | 606/107 |
| 5,190,552 | 3/1993 | Kelman | 606/107 |
| 5,275,604 | 1/1994 | Rheinish et al. | 606/107 |
| 5,494,484 | 2/1996 | Feingold | 606/107 |
| 5,499,987 | 3/1996 | Feingold | 606/107 |
| 5,503,848 | 4/1996 | Perbellini et al. | 424/488 |
| 5,523,093 | 6/1996 | Della Valle et al. | 424/444 |
| 5,561,905 | 10/1996 | Sherman | 30/280 |
| 5,616,148 | 4/1997 | Eagles et al. | 606/107 |
| 5,620,450 | 4/1997 | Eagles et al. | 606/107 |
| 5,650,164 | 7/1997 | Della Valle et al. | 424/422 |
| 5,653,715 | 8/1997 | Reich et al. | 606/107 |
| 5,653,753 | 8/1997 | Brady et al. | 623/3 |
| 5,658,331 | 8/1997 | Della Valle et al. | 623/15 |
| 5,709,877 | 1/1998 | Della Valle et al. | 424/444 |
| 5,711,317 | 1/1998 | McDonald | 606/107 |
| 5,735,858 | 4/1998 | Makker et al. | 606/107 |
| 5,766,182 | 6/1998 | McDonald | 606/107 |
| 5,776,139 | 7/1998 | McDonald | 606/107 |

FOREIGN PATENT DOCUMENTS

| | | |
|---|---|---|
| 2224214A | 5/1990 | United Kingdom . |
| WO 96/29956 | 10/1996 | WIPO . |
| WO 98/15244 | 4/1998 | WIPO . |

*Primary Examiner*—Paul J. Hirsch
*Attorney, Agent, or Firm*—Jeffrey S. Schira

[57] ABSTRACT

A hinged, relatively rigid substrate on which a foldable IOL is held by a thin, relatively non-elastic film of esterified hyaluronate. When the substrate is folded along the hinge, the film covering the IOL causes the IOL to also fold along the hinge. The folded lens can then be placed in a conventional IOL injector handpiece that has been modified to include a cutter or the like to separate the film-encased IOL from the substrate prior to injection into the eye.

15 Claims, 3 Drawing Sheets

INTRAOCULAR LENS INJECTION SYSTEM

This invention relates to foldable intraocular lenses (IOLs) and more particularly to folding devices used to inject IOLs into an eye.

BACKGROUND OF THE INVENTION

The human eye in its simplest terms functions to provide vision by transmitting and refracting light through a clear outer portion called the cornea, and further focusing the image by way of the lens onto the retina at the back of the eye. The quality of the focused image depends on many factors including the size, shape and length of the eye, and the shape and transparency of the cornea and lens.

When trauma, age or disease cause the lens to become less transparent, vision deteriorates because of the diminished light which can be transmitted to the retina. This deficiency in the lens of the eye is medically known as a cataract. The typical treatment for this condition is surgical removal of the lens and implantation of an artificial intraocular lens or IOL.

While early IOLs were made from hard plastic, such as polymethylmethacrylate (PMMA), soft, foldable IOLs made from silicone, soft acrylics and hydrogels have become increasingly popular because of the ability to fold or roll these soft lenses and insert them through a smaller incision. Several methods of rolling or folding the lenses are used. One popular method is an injector cartridge that folds the lenses and provides a relatively small diameter lumen through which the lens may be pushed into the eye, usually by a soft tip plunger. A commonly used injector cartridge design is illustrated in U.S. Pat. No. 4,681,102 (Bartell), the entire contents of which is incorporated herein by reference, and includes a split, longitudinally hinged cartridge. Similar designs are illustrated in U.S. Pat. Nos. 5,494,484 and 5,499,987 (Feingold) and 5,616,148 and 5,620,450 (Eagles, et al.), the entire contents of which are incorporated herein by reference. Several hinge-less cartridges are known. See, for example, U.S. Pat. No. 5,275,604 (Rheinish, et al.) and 5,653,715 (Reich, et al.), the entire contents of which are incorporated herein by reference.

These prior art cartridges all have relatively rigid walls surrounding a smooth, round or elliptical bore that is symmetric about the longitudinal axis. The rigid walls work to fold and compress the IOL prior to insertion. Depending on the IOL material used, friction between the rigid walls and the IOL can make it difficult or impossible to express the IOL from the cartridge without damage to the IOL or delicate ocular tissue. To reduce friction, a common practice is to apply a viscoelastic agent or other biocompatible lubricant to the IOL and/or bore of the cartridge. While the application of a lubricating viscoelastic agent works well with some silicone and hydrogel materials, other materials such as soft acrylics can be very hydrophobic, making it difficult to lubricate these lenses with conventional water-based viscoelastic solutions.

Another limitation of commercially available prior art lens cartridges is that they are all packaged separately from the IOL, requiring the surgeon or operating room staff to load the IOL into the cartridge thereby introducing the opportunity for mishandling or damage to the IOL.

Accordingly, a need continues to exist for an improved IOL injection system that facilitates the loading and expression of soft lenses.

BRIEF SUMMARY OF THE INVENTION

The present invention improves upon prior art injector cartridges by providing a hinged, relatively rigid substrate on which a foldable IOL is held by a thin, relatively non-elastic film of esterified hyaluronate. When the substrate is folded along the hinge, the film covering the IOL causes the IOL to also fold along the hinge. The folded lens can then be placed in a conventional IOL injector handpiece that has been modified to include a cutter or the like to separate the film-encased IOL from the substrate prior to injection into the eye.

It is accordingly an objective of the present invention to provide a lens system suitable for use with foldable IOLs.

It is a further objective of the present invention to provide a lens injector system that uses a thin, lubricious film to facilitate expression of the IOL into the eye.

It is a further objective of the present invention to provide a lens injector system having a relatively rigid substrate that can be folded along a hinge.

Still another objective of the present invention is to provide a lens injector system which obviates the need for direct handling of the IOL when loading the IOL into the injector handpiece.

Other objectives, features and advantages of the present invention will become apparent with reference to the drawings, and the following description of the drawings and claims.

DETAILED DESCRIPTION OF THE INVENTION

Figure 2:
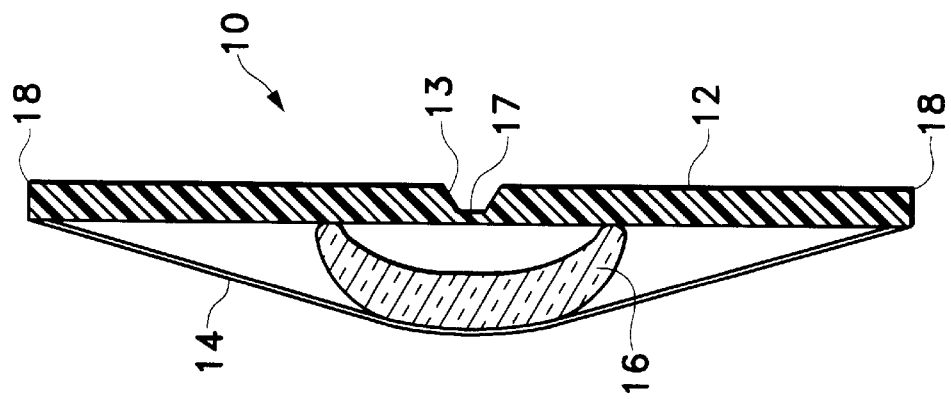
FIG. 2 a cross-sectional view of the intraocular lens injection system folder taken at line 2—2 in FIG. 1.
Figure 1:
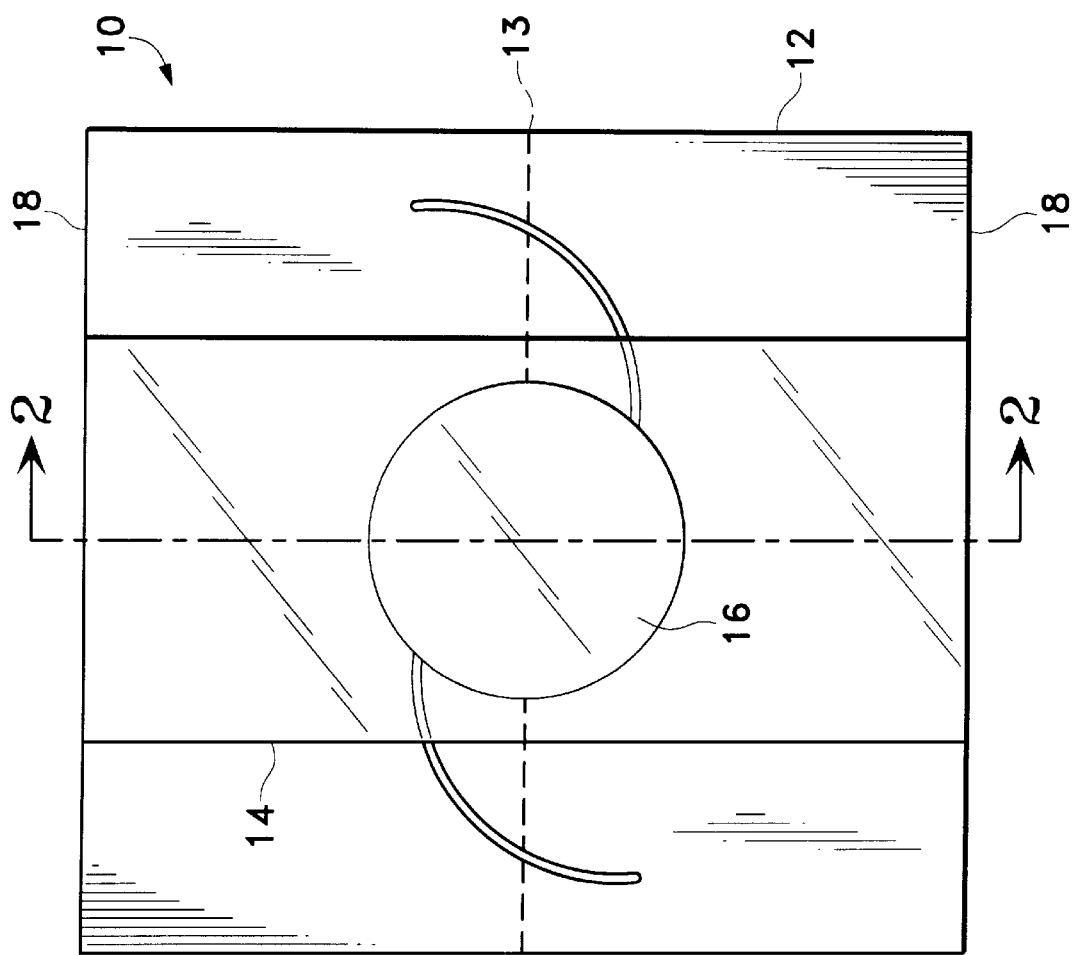
FIG. 1 is a top plan view of one embodiment of the intraocular lens injection system folder of the present invention.
Figure 3:
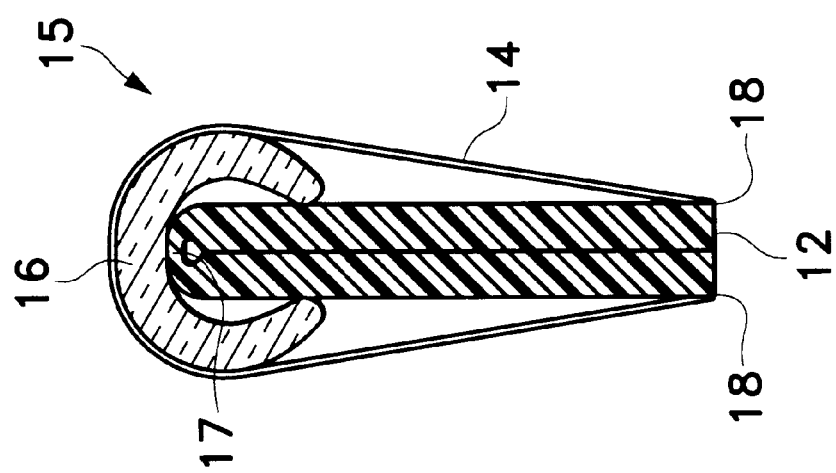
FIG. 3 is a cross-sectional view of the intraocular lens injector system folder illustrated in FIGS. 1 and 2 with the substrate and the lens shown in the folded position.
Figure 5:
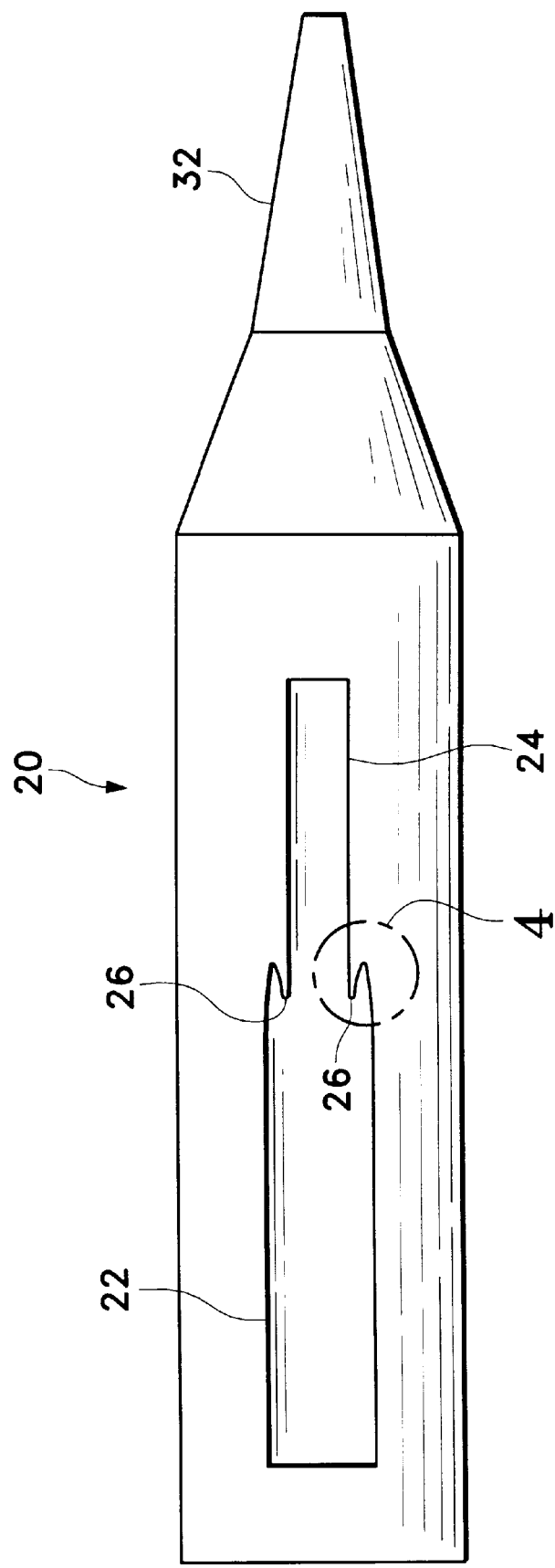
FIG. 5 is a top plan view of one embodiment of a intraocular lens injection system handpiece of the present invention.

As best seen in FIGS. 1, 2 and 3, folder 10 of the present invention generally includes substrate 12, and retaining/folding film 14. Substrate 12 may be made of any suitable material, such as a thermoplastic (e.g., polypropylene), may contain a lubricity enhancing agent such as those disclosed in U.S. Pat. No. 5,716,364, the entire contents of which is incorporated herein by reference, and contains hinge 17, preferably a living hinge created by hinge-forming notch or cut 13. Film 14 may be any suitable biocompatible film, but polysaccharide films, such as those described in U.S. Pat. Nos. 5,709,877, 5,658,331, 5,523,093 and 5,503,848, the entire contents of which are incorporated herein by reference, are preferred, with transparent esterified hyaluronate being most preferred. Alternatively, substrate 12 may also be covered by film 14 or substrate 12 may contain a lubricious coating such as those described in U.S. Pat. Nos. 4,487,865, 4,500,676, 4,663,233, 4,801,475, 4,959,074, 5,023,114 and 5,037,677, the entire contents of which are incorporated herein by reference.

IOL 16 is held on substrate 12 centered over notch 13 by film 14, which is applied over IOL 16 and attached or bonded to substrate 12 at or near edges 18 by any suitable method to hold IOL 16 firmly in place. In use, edges 18 are pivoted toward each other and away from IOL 16 about notch 13, thereby folding substrate 12 roughly in half. Pivoting edges 18 toward each other pulls film 14 more tightly over IOL 16, causing IOL 16 to fold about notch 13, as best seen in FIG. 3. Prior to loading folded IOL/film/substrate combination 15 into handpiece 20, film 14 may be moistened, preferably with sterile irrigating solution, to maximize its lubricious character. Edges 18 may also be roughened or thickened in order to provide a better grip and/or to ensure proper insertion depth of IOL 16 into handpiece 20.

Figure 4:
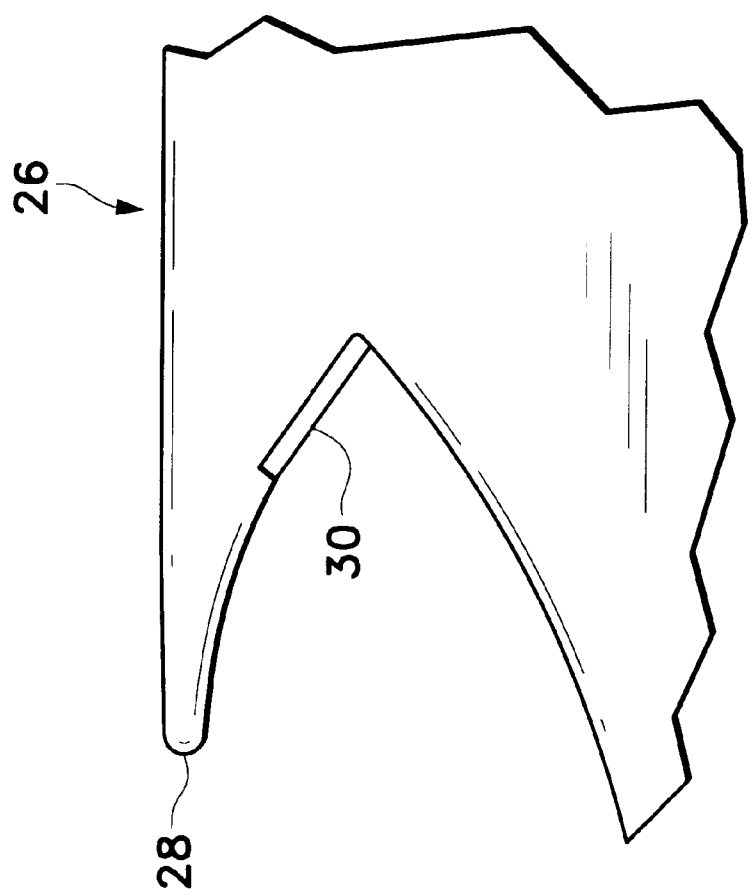
FIG. 4 is an enlarged partial view of a cutter that can be used with the present intraocular lens injection system handpiece taken at circle 4 in FIG. 5.

To insert IOL 16 into an eye, handpiece 20 may be used. Handpiece 20 contains large slot 22 into which combination 15 may be inserted. Combination 15 is held tightly in the folded position within handpiece 20 by sliding combination 15 into adjoining narrower slot 24, the width of which is sized to hold combination 15 tightly (approximately the same as twice the thickness of substrate 12). In order to separate film 14 from substrate 12, cutter 26, preferably integrally situated on handpiece 20 near the junction of slot 22 and slot 24, as best seen in FIG. 4, is adapted to cut through film 14 on at least one side of combination 15 without contacting IOL 16. Cutter 26 may contain blunt tip 28 and cutting blade 30. Sliding combination 15 into small slot 24 allows tip 28 to enter the space between film 14 and substrate 12 and force film 14 toward blade 30. Blade 30 cuts film 14, thereby separating film 14 from substrate 12 and allowing IOL 16, having an exterior surface still covered by film 14, to be pushed down injection tube 32 by an appropriate plunger device (not shown). Blunt tip 28 helps prevent damage to IOL 16 or to substrate 12 when combination 15 is moved between slot 22 and slot 24, and may act as a clip to ensure that combination 15 is properly and securely positioned in slot 24 prior to expulsion of IOL 16.

While certain embodiments of the present invention have been described above, these descriptions are given for purposes of illustration and explanation. Variations, changes, modifications and departures from the systems and methods disclosed above may be adopted without departure from the scope or spirit of the present invention.

I claim:

1. An intraocular lens injection system, comprising:
   a) a relatively rigid substrate, the substrate having at least two edges and a hinge; and
   b) a foldable intraocular lens held on the substrate by a retaining/folding film, the film being applied over the intraocular lens and attached to the substrate.

2. The system of claim 1, wherein the hinge is a living hinge.

3. The system of claim 1, wherein the hinge is created by a hinge forming notch.

4. The system of claim 1, wherein the film is a polysaccharide film.

5. The system of claim 4, wherein the polysaccharide film is esterified hyaluronate.

6. The system of claim 1, wherein the intraocular lens is centered over the hinge.

7. The system of claim 1, wherein the intraocular lens is a soft acrylic lens.

8. The system of claim 1, further comprising a handpiece having a slot for receiving the substrate and a cutter for separating the film from the substrate.

9. A method of folding a foldable intraocular lens, comprising the steps of:
   a) placing the foldable intraocular lens on a relatively rigid substrate, the substrate having at least two edges and a hinge, so that the intraocular lens is over the hinge;
   b) holding the foldable intraocular lens on the substrate by a retaining/folding film, the film being applied over the intraocular lens and attached to the substrate; and
   c) pivoting the edges of the substrate toward each other about the hinge, thereby pulling the film more tightly over the intraocular lens and causing the intraocular lens to fold about the hinge.

10. The method of claim 9, wherein the hinge is a living hinge.

11. The method of claim 9, wherein the hinge is created by a hinge forming notch.

12. The method of claim 9, wherein the film is a polysaccharide film.

13. The method of claim 12, wherein the polysaccharide film is esterified hyaluronate.

14. The method of claim 9, wherein the intraocular lens is centered over the hinge.

15. The method of claim 9, wherein the intraocular lens is a soft acrylic lens.

* * * * *